US00PP18648P2

(12) United States Plant Patent
Stolwijk

(10) Patent No.: US PP18,648 P2
(45) Date of Patent: Mar. 25, 2008

(54) ***CLEMATIS* PLANT NAMED 'STOLWIJK GOLD'**

(50) Latin Name: *Clematis alpina*
Varietal Denomination: Stolwijk Gold

(75) Inventor: Hans Stolwijk, Reeuwijk (NL)

(73) Assignees: Q.C. Stolwijk + Co. B.V., Boskoop (NL); Rijnbeek + Son B.V., Boskoop (NL)

( * ) Notice: Subject to any disclaimer, the term of this patent is extended or adjusted under 35 U.S.C. 154(b) by 0 days.

(21) Appl. No.: 11/583,610

(22) Filed: Oct. 19, 2006

(51) Int. Cl.
*A01H 5/00* (2006.01)

(52) U.S. Cl. ..... Plt./228

(58) Field of Classification Search ..... Plt./228
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Clematis* plant named 'Stolwijk Gold', characterized by its upright and vining plant habit; uniquely yellow green-colored foliage; freely flowering habit; and violet blue-colored flowers.

2 Drawing Sheets

Botanical designation: *Clematis alpina.*
Cultivar denomination: 'Stolwijk Gold'.

BACKGROUND OF THE INVENTION

The present invention relates to a new and distinct cultivar of *Clematis,* botanically known as *Clematis alpina* and hereinafter referred to by the name 'Stolwijk Gold'.

The new *Clematis* is a naturally-occurring whole plant mutation of an unnamed selection of *Clematis alpina,* not patented. The new *Clematis* was discovered and selected by the Inventor as a single plant in a population of plants of the parent selection in a controlled environment in Boskoop, The Netherlands in May, 2001. The new *Clematis* was selected based on its unique yellowgreen-colored leaves.

Asexual reproduction of the new cultivar by cuttings in Boskoop, The Netherlands, since May, 2001, has shown that the unique features of this new *Clematis* are stable and reproduced true to type in successive generations.

SUMMARY OF THE INVENTION

Plants of the cultivar Stolwijk Gold have not been observed under all possible environmental conditions. The phenotype may vary somewhat with variations in environment such as temperature and light intensity without, however, any variance in genotype.

The following traits have been repeatedly observed and are determined to be the unique characteristics of 'Stolwijk Gold'. These characteristics in combination distinguish 'Stolwijk Gold' as a new and distinct cultivar:

1. Upright and vining plant habit.
2. Uniquely yellow green-colored foliage.
3. Freely flowering habit.
4. Violet blue-colored flowers.

Plants of the new *Clematis* differ primarily from plants of the parent selection in leaf color as plants of the parent selection have solid green-colored leaves.

Plants of the new *Clematis* can be compared to plants of the *Clematis* cultivar Multi Blue, not patented. In side-by-side comparisons conducted by the Inventor in Boskoop, The Netherlands, plants of the new *Clematis* differed primarily from plants of the cultivar Multi Blue in leaf color as plants of the cultivar Multi Blue had solid green-colored leaves.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Clematis.*

The photograph on the first sheet comprises a side perspective view of a typical flowering plant of 'Stolwijk Gold' grown in a container.

The photograph at the top of the second sheet is a close-up view of a typical flower of 'Stolwijk Gold'.

The photograph at the bottom of the second sheet is a close-up view of a typical leaf of 'Stolwijk Gold'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photograph and following description were grown under conditions which closely approximate commercial production conditions during the summer in an outdoor nursery in Boskoop, The Netherlands for about two years. During the production of the plants, day temperatures ranged from 12° C. to 32° C. and night temperatures ranged from 7° C. to 14° C.

Botanical classification: *Clematis alpina* cultivar Stolwijk Gold.

Parentage: Naturally-occurring whole plant mutation of an unnamed selection of *Clematis alpina,* not patented.

Propagation:

*Type.*—By cuttings.

*Time to produce a rooted young plant, summer.*—About 21 days at 20° C.

*Time to produce a rooted young plant, winter.*—About 40 days at 12° C.

*Root description.*—Fine, fibrous; yellow brown in color.

*Rooting habit.*—Freely branching; dense.

Plant description:

*Form.*—Perennial. Upright and vining plant habit. Moderately vigorous growth habit.

*Plant height.*—About 126.5 cm.

*Plant width.*—About 36.5 cm.

*Lateral branch description.*—Length: About 18.6 cm. Diameter: About 2 cm. Internode length: About 7.9 cm. Strength: Strong. Texture: Moderately pubescent. Color, young: 183A. Color, mature: 199B to 199C, becoming closer to 200A.

Foliage description:

*Arrangement.*—Opposite, compound with three leaflets.

*Length, leaf.*—About 6.5 cm.

*Length, terminal leaflet.*—About 4.2 cm.

*Length, lateral leaflets.*—About 4.1 cm.

*Width, leaf.*—About 6.7 cm.

*Width, terminal leaflet.*—About 3.6 cm.

*Width, lateral leaflets.*—About 2.8 cm.

*Shape, leaf.*—Three-parted; broadly ovate in outline.

*Shape, leaflets.*—Trifoliate; ovate in outline.

*Apex, leaflets.*—Narrowly acute.

*Base, leaflets.*—Cordate.

*Margin, leaflets.*—Serrate.

*Texture, leaflets, upper and lower surfaces.*—Smooth, glabrous.

*Venation pattern, leaflets.*—Pinnate.

*Color, leaflets.*—Developing foliage, upper surface: 151B to 151C, becoming closer to 154A; towards the margins, close to 187A. Developing foliage, lower surface: N144A to N144B. Fully expanded foliage, upper surface: 6B to 6C flushed with 144B; 6B to 6C flushed with 144A. Fully expanded foliage, lower surface: 4C flushed with 144B to 144C; venation, 144A.

*Petiole length.*—About 5.7 cm.

*Petiole diameter.*—About 1 mm.

*Petiole color, upper surface.*—187A.

*Petiole color, lower surface.*—146D.

Flower description:

*Flower arrangement and shape.*—Single rotate terminal flowers; flowers drooping. Freely flowering, about 45 flowers develop per plant.

*Natural flowering season.*—Continuous flowering from spring to early autumn in The Netherlands.

*Flower longevity on the plant.*—About ten days; flowers not persistent.

*Fragrance.*—None detected.

*Flower buds.*—Length: About 1.9 cm. Diameter: About 9 mm. Shape: Ovate. Color: 93C.

*Flowers.*—Diameter: About 5.6 cm. Depth (height): About 2.4 cm.

*Petals.*—None observed.

*Sepals.*—Arrangement: Four to eight in a single whorl. Length: About 2.8 cm. Width: About 9 mm. Shape: Lanceolate to narrowly ovate. Apex: Acute. Margin: Entire. Texture, upper and lower surfaces: Smooth, glabrous. Color: When opening, upper and lower surfaces: 93C. Fully opened, upper and lower surfaces: 93C, becoming closer to 94B.

*Sepaloids.*—Arrangement: About 10 to 14 in several whorls. Length: About 1.7 cm to 2.6 cm. Width: About 4 mm to 5 mm. Shape: Narrowly elliptic to narrowly obovate. Apex: Acute. Margin: Entire. Texture, upper and lower surfaces: Densely pubescent. Color, upper and lower surfaces: 94B; more inwardly sepals, 92B, towards the apex, 3C.

*Peduncles.*—Length: About 6.1 cm. Diameter: About 1.5 cm. Strength: Strong. Texture: Smooth, glabrous. Color: 187A.

*Reproductive organs.*—Stamens: Quantity per flower: About 45. Filament length: About 1.2 cm. Filament color: 145C. Anther shape: Linear. Anther length: About 2 mm. Anther color: 4D. Pollen amount: Scarce. Pollen color: 4D. Pistils: Quantity per flower: About 45. Pistil length: About 9 mm. Stigma shape: Conical, narrow. Stigma color: 155C. Style length: About 6 mm. Style color: 145D. Ovary color: 157A.

*Seed/fruit.*—Seed and fruit production has not been observed.

Disease/pest resistance: Plants of the new *Clematis* have not been noted to be resistant to pathogens and pests common to *Clematis.*

Garden performance: Plants of the new *Clematis* have exhibited good tolerance to rain and wind and have been observed to be suitable for USDA Zone 5 and tolerate high temperatures to about 35° C.

It is claimed:

1. A new and distinct *Clematis* plant named 'Stolwijk Gold' as illustrated and described.

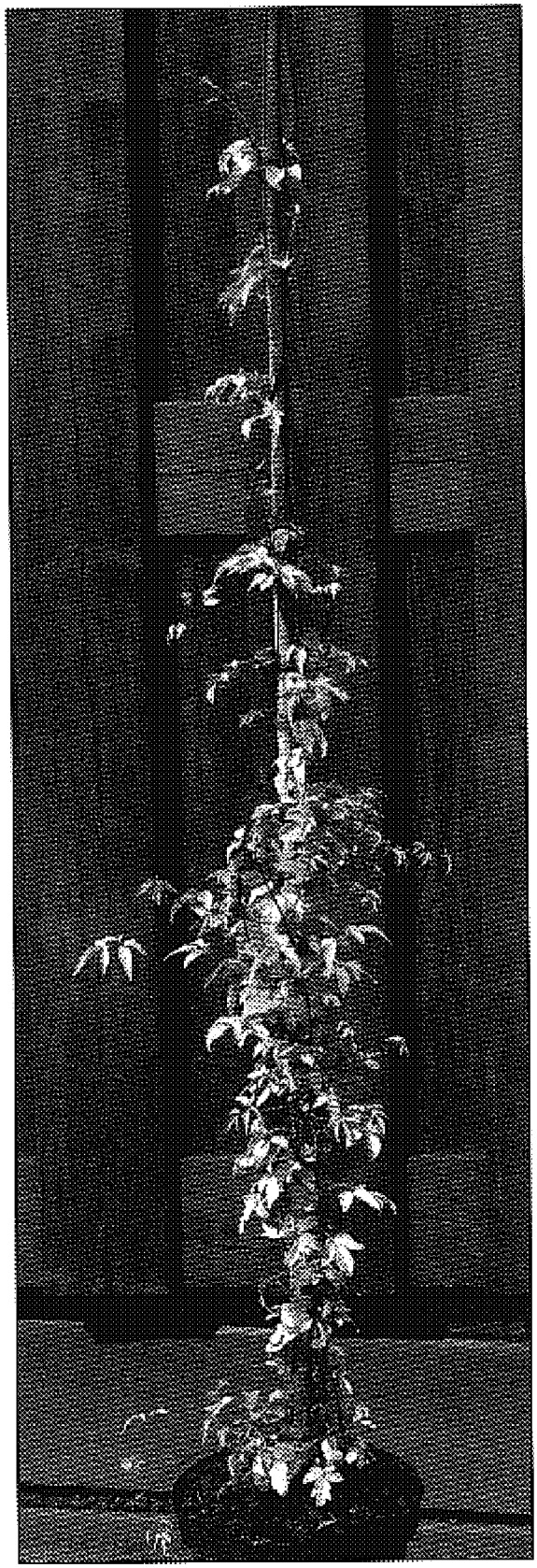

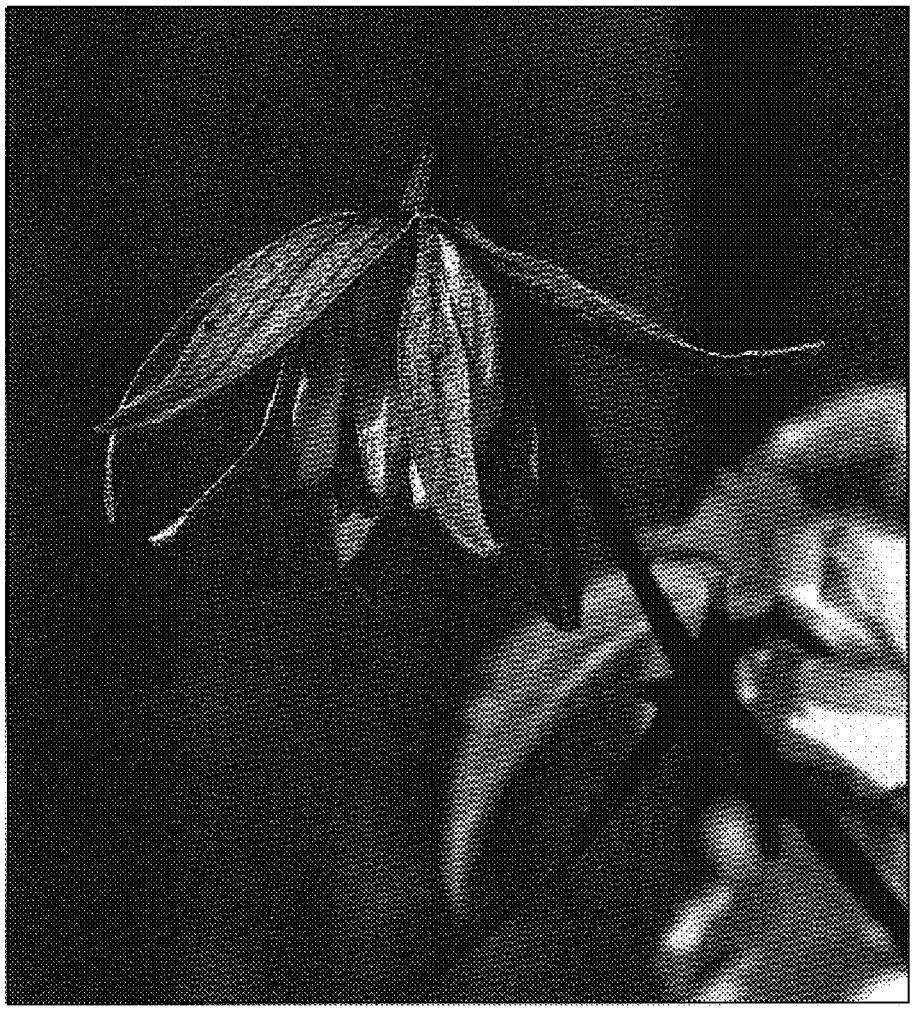
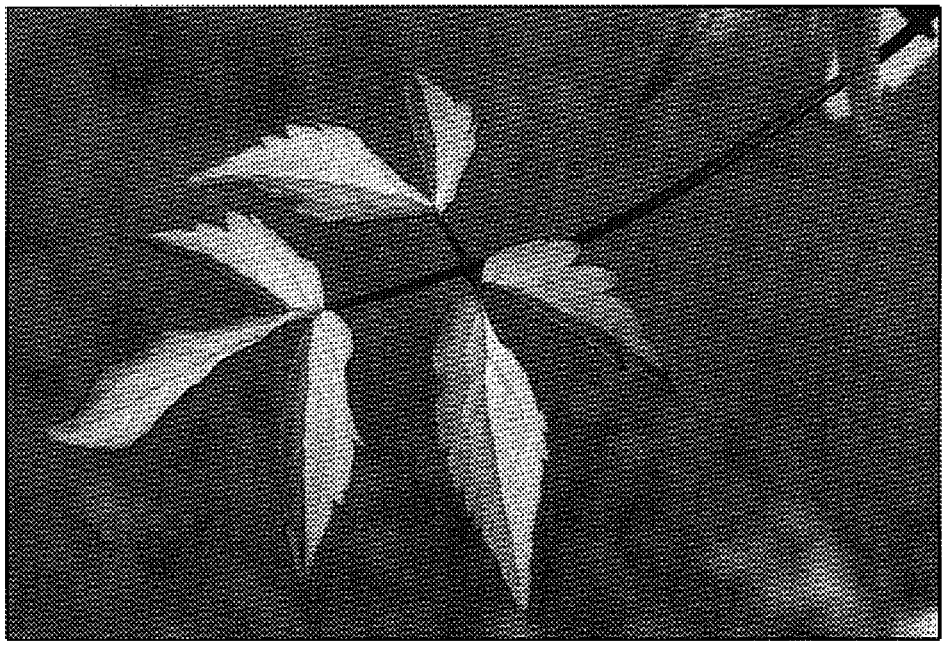

* * * * *